United States Patent [19]
Loge

[11] 3,936,940
[45] Feb. 10, 1976

[54] DENTAL HANDTOOL

[75] Inventor: Hans Loge, Biberach an der Riss, Germany

[73] Assignee: Kaltenbach & Voight, Germany

[22] Filed: July 3, 1974

[21] Appl. No.: 485,758

[30] Foreign Application Priority Data
July 6, 1973 Germany.............................. 2334448

[52] U.S. Cl. .................................................. 32/26
[51] Int. Cl.² .......................................... A61C 1/08
[58] Field of Search........................... 32/26, 27, 28

[56] References Cited
UNITED STATES PATENTS

| | | |
|---|---|---|
| 3,252,719 | 5/1966 | Borden .................... 32/27 |
| 3,381,378 | 5/1968 | Lawrence et al. ...................... 32/27 |
| 3,815,240 | 6/1974 | Loge ..................................... 32/27 |

FOREIGN PATENTS OR APPLICATIONS

| | | |
|---|---|---|
| 1,107,890 | 5/1961 | Germany ............................... 32/27 |

Primary Examiner—Louis G. Mancene
Assistant Examiner—J. Q. Lever
Attorney, Agent, or Firm—Haseltine, Lake & Waters

[57] ABSTRACT

A dental handtool in which an extended sleeve has at its center, a driving shaft for rotary movement of the tool used for dental treatment. The driving shaft is at one end of the sleeve, and a freely rotating driving part is attached to the handtool at the opposite end of the sleeve. A coolant pipe between the driving part and the handtool, feeds coolant to the treatment area of the dental tool.

8 Claims, 3 Drawing Figures

DENTAL HANDTOOL

BACKGROUND OF THE INVENTION

The invention concerns a dental handtool with an extended handtool sleeve, in the center of which a driving shaft is located for the rotary movement of a tool for dental treatment. The tool is fitted at one end of the sleeve, and at the opposite end of the sleeve to which the tool is fitted, a driving part can be fitted to the handtool. The driving part is essentially free to rotate, and between the driving part and the handtool a separable coolant pipe is provided to feed coolant to the area of the dental treatment tool.

Such handtools, heretofore, are known from a leaflet of the applicant's product literature PR-Nr. 7230/4-III.71, page 3 and 4. Here the driving part is provided with a discharge pipe piece and with an inlet pipe piece on the handtool for a flexible coolant pipe. Should one now wish to place a different handtool onto the driving part, the coolant pipe must first be freed from the previously used handtool, and after connecting the new handtool, the coolant pipe must again be pushed onto the inlet pipe stub. In addition, even with an excessive length of flexible coolant pipe, free rotation of the handtool against the driving part of more than 360° is not possible, because the coolant pipe winding itself around the handtool or the driving part by the rotation, blocks further turning by a rotational path depending on the length of the coolant pipe.

Accordingly, an object of the present invention is to produce a dental handtool of the foregoing character, in which an essential, required free rotation between the handtool and the driving part is obtained and special hand operations are avoided when connecting or disconnecting, the coolant pipe sections in the driving part and in the handtool.

SUMMARY OF THE INVENTION

The object is achieved in accordance with the invention, with the coolant pipe section running within the driving part. In the connected condition, it protrudes out of a surface of the driving part resting against the handtool, and there runs out into a ring or annular channel provided on the driving part and/or on the handtool, from where the coolant pipe section inside the handtool protrudes.

This produces the assurance, that without any special hand operation, a connection is immediately made between the coolant pipe section inside the driving part and the coolant pipe section inside the handtool. The ring channel thus permits an unlimited free rotation around the axis of the essentially cylindrical-shaped, extended handtool between the handtool and the driving part, provided it is constructed as a closed ring.

Sometimes an unlimited free rotation is not desired. It then suffices, when after a further embodiment of the invention, the ring channel is formed in the shape of an open ring or sub-divided into several sections.

So that no measures need be taken when connecting, because of the necessary sealing off of the ring channel in order to ensure a special tight fit of the surface of the driving part and the handtool which mate, it is provided that on both sides of the ring channel sealing elements e.g. O-rings are present.

A special suitable form of construction regarding the practically automatic adjusted connection of the coolant pipe resides in the feature that the coolant pipe section inside the driving part, before its emergence, is attached to a guide connecting piece of the drive part inserted in the wall of a connecting opening of the handtool, and emerges out of this wall radial to the guide pipe stub.

On the other hand it is also possible, that before its emergence, the coolant pipe section inside of the driving part, is arranged in a sleeve of the driving part, which overlaps the handtool with its end, and emerges radial from the sleeve. A further possibility exists, in that the coolant pipe section inside the driving part emerges from the face side of the driving part, which faces the handtool.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
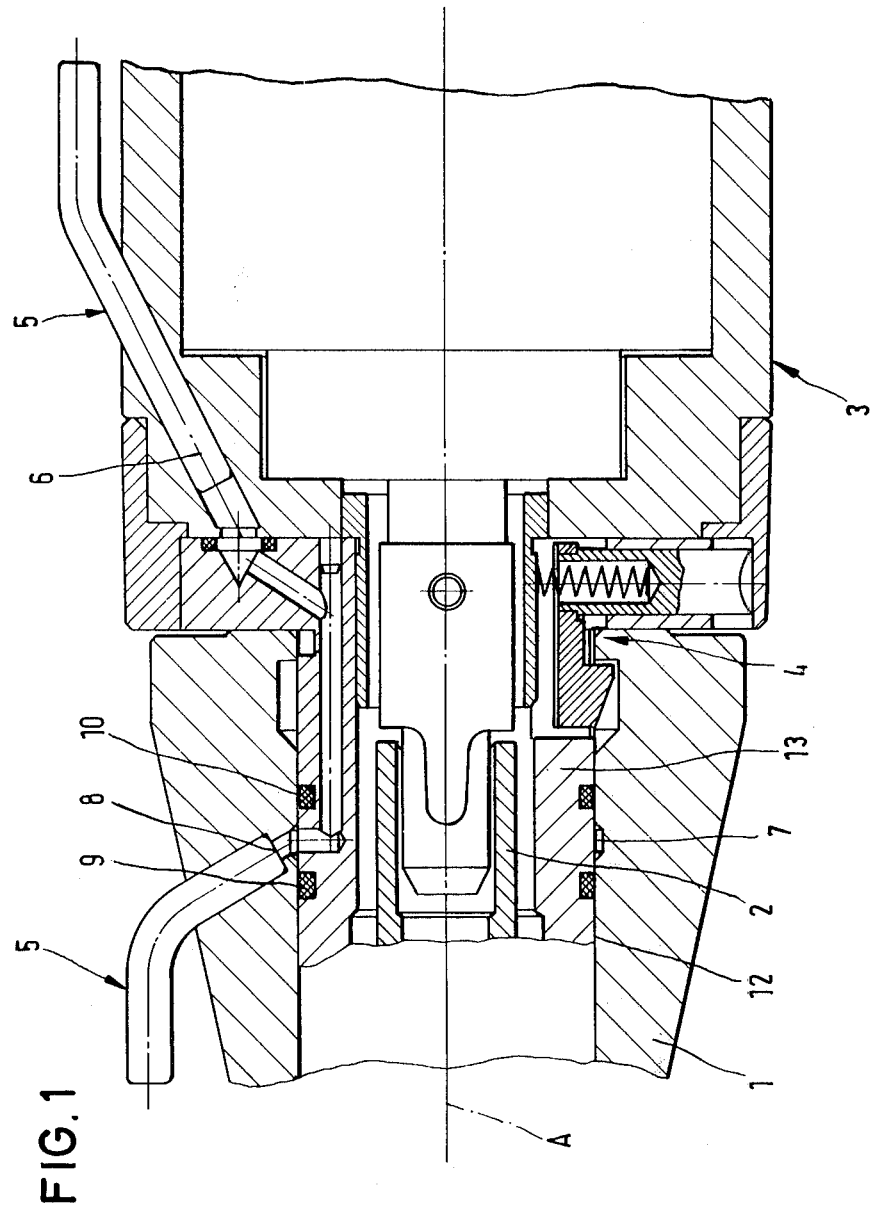
FIG. 1 is a sectional elevational view of a dental handtool connected freely rotating to a driving part, with the front or rear ends of the connected parts omitted in the interest of clarity.

Referring to the drawing, the cylindrical handtool sleeve of an extended dental handtool is designated by 1 in the drawing. Within this sleeve, the driving shaft 2 for the rotary movement of a tooth treatment tool e.g. of a drill, is centrally located. The known or conventional bearing of the driving shaft and the also known dental tool are not illustrated for the sake of clarity. On the sleeve end opposite the tool end i.e. on the right hand end of the handtool sleeve 1 in the drawing, is a driving part referenced in general by 3, and is freely rotatably connected to the handtool. The coupling devices in general referenced by 4, are provided for the connection, and are here not described in detail. Between the driving part 3 and the handtool sleeve 1 is a coolant pipe generally referenced by 5, to feed coolant to the area of the dental tool.

The coolant pipe section 6 inside of the driving part 3, emerges on a surface of the driving part 3 which butts against a corresponding surface of the handtool sleeve 1 in the connected state, and runs out into a ring channel 7, from where the coolant pipe section 8 inside the handtool sleeve starts out. In the case of FIGS. 1 and 3, the ring channel is on the handtool and in the case of FIG. 2 in the driving part 3. On both sides of the channel 7 is fitted a sealing ring 9, 10. The sealing rings 9, 10 are located in corresponding grooves, which are arranged within the inside wall of the handtool sleeve 1 (FIG. 1), or within the inside wall of a sleeve 11 of the driving part 3 (FIG. 2) with its end overlapping the handtool sleeve 1, or in the face wall of the driving part 3 (FIG. 3).

In the form of construction of FIG. 1, the coolant pipe section 6 within the inside of the drive part 3 is before its emergence, arranged in a guide connecting piece 13 inserted in the wall of a connecting opening 12 of the handtool sleeve 1. The coolant pipe section 6 emerges there radial to the guide connecting piece 13 from its wall to the outside, and there runs out into the ring channel 7.

Figure 2:
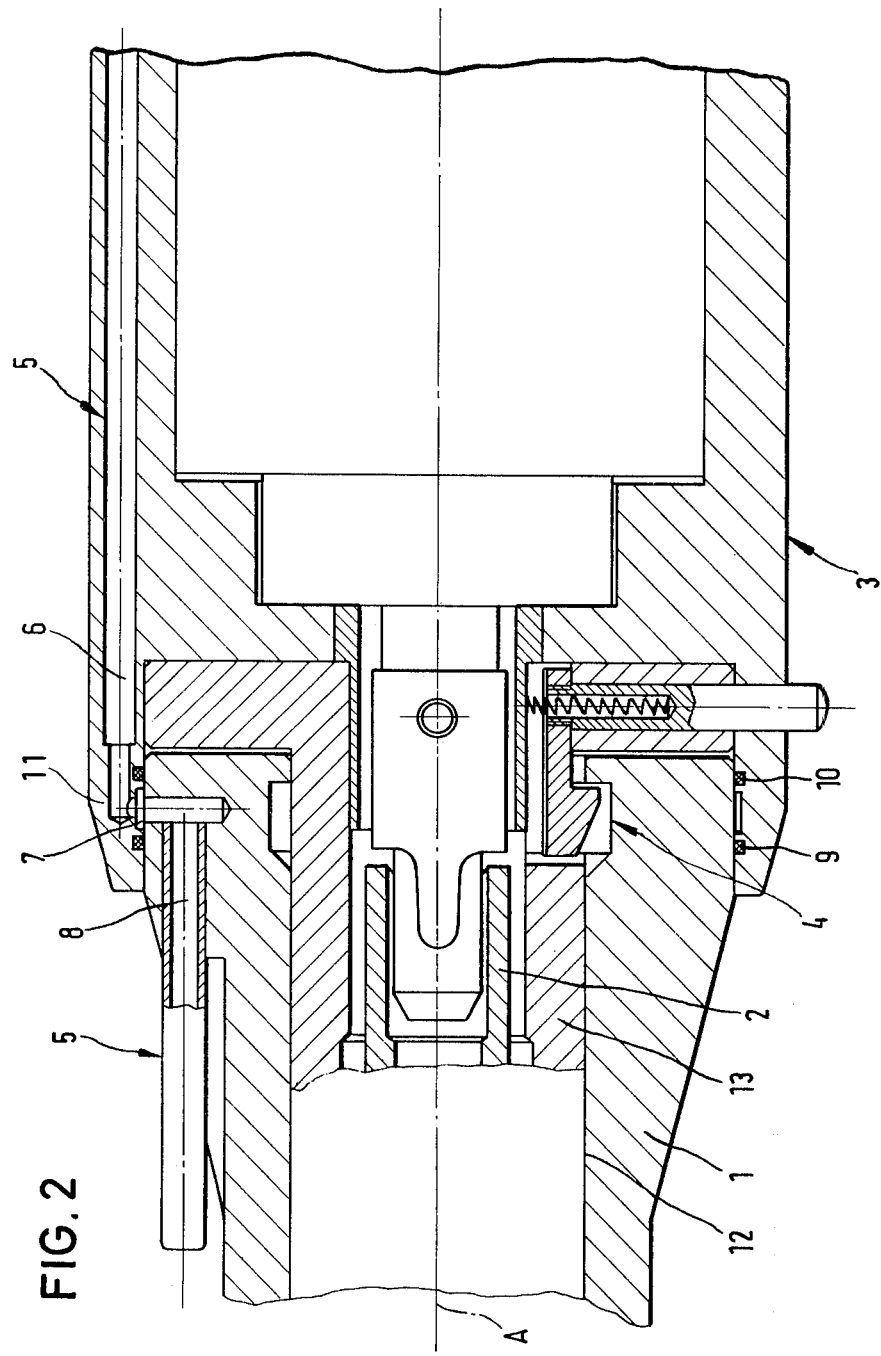
FIG. 2 is a sectional elevational view of another embodiment of FIG. 1.
Figure 3:
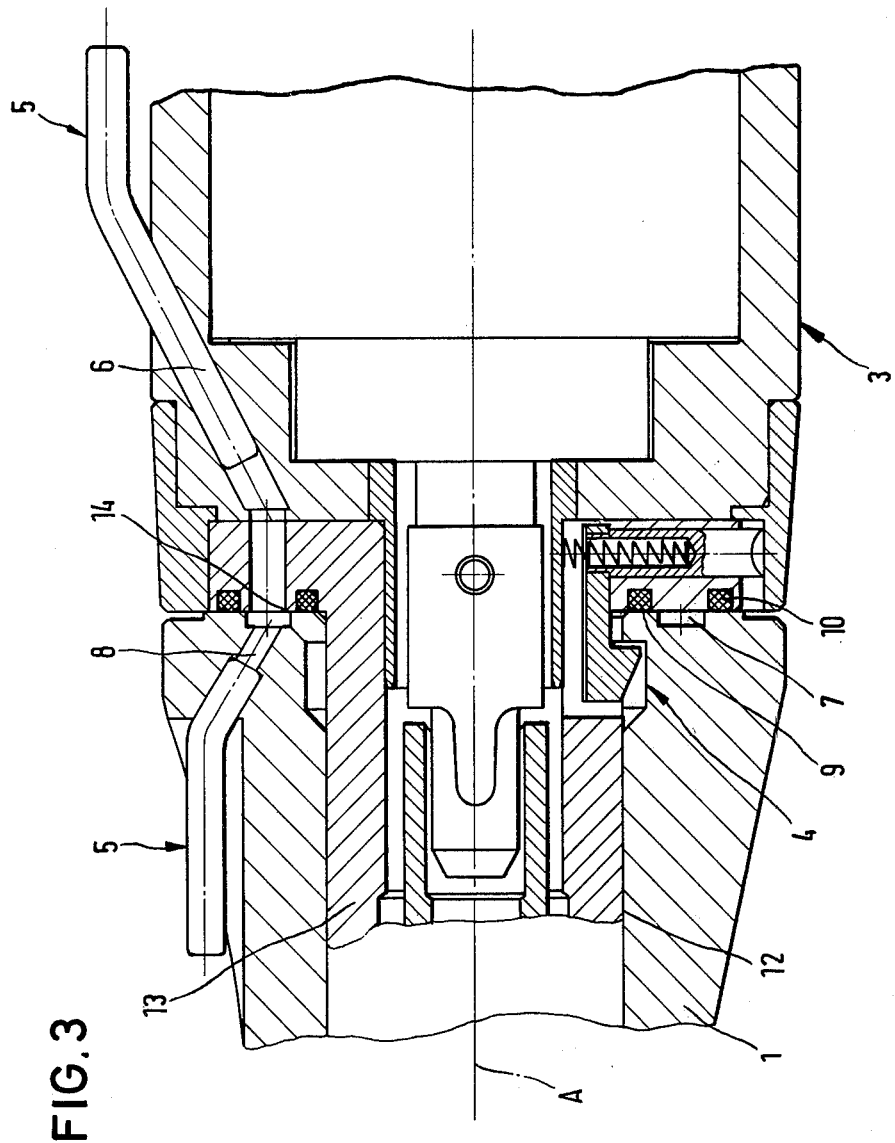
FIG. 3 is a sectional elevational view of a further embodiment of FIG. 1.

In the form of construction to FIG. 2 the coolant pipe section 6 within the inside of the drive part 3 emerges out of the face side 14 of the drive part 3, facing the handtool 1, and there runs out axial, i.e. parallel to the axis A of the handtool sleeve 1 into the ring channel 7.

The coolant pipe section 8 in the inside of the handtool can, as not illustrated, run along the inside up to the handtool point showing the treatment tool. As, however, the coolant pipe in this section causes no real trouble if it runs to the outside, the coolant pipe section 8 of the handtool sleeve 1, can also as illustrated in the drawing, emerge to the outside and run parallel to the axis A to the front, where it then passes by one of the known methods to the squirting section directed to the tool tip.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

I claim:

1. A dental handtool comprising, in combination, an extended hand sleeve; a driving shaft located at the center of said sleeve for rotary movement of a tool for dental treatment, said tool being at one end of said sleeve, a freely rotating driving part disconnectably attached to the handtool at the opposite end of said sleeve; a coolant pipe for feeding coolant to the region of said dental tool, said coolant pipe having a first coolant section inside said driving part and having a second section inside said sleeve; a ring channel; said coolant sections being disconnectably coupled by said ring channel when in the connected state; sealing elements on two sides of said ring channel, the coolant section inside said driving part entering said ring channel radially from said driving part.

2. The dental handtool as defined in claim 1, including a guide connecting piece, a wall having an opening for insertion of said connecting piece, said first coolant section inside said driving part being fitted to said guide connecting piece before emerging, said first coolant section emerging out of said wall radial to said guide connecting piece; a sleeve on said driving part, said second coolant section arranged in said sleeve before emerging and overlapping the handtool with its end, said second coolant section emerging radially out of said sleeve.

3. The dental handtool as defined in claim 2, wherein said ring channel comprises substantially an open ring, said ring channel being sub-divided into a plurality of sections, said first coolant section inside said driving part emerging from the side of said driving part facing the handtool.

4. The dental handtool as defined in claim 1, wherein said ring channel comprises substantially an open ring.

5. The dental handtool as defined in claim 1, wherein said ring channel is sub-divided into several sections.

6. The dental handtool as defined in claim 1, including a guide connecting piece; a wall having an opening for insertion of said connecting piece, said first coolant section inside said driving part being fitted to said guide connecting piece before emerging, said first coolant section emerging out of said wall radial to said guide connecting piece.

7. The dental handtool as defined in claim 1, including a sleeve on said driving part, said second coolant section arranged in said sleeve before emerging and overlapping the handtool with its end, said second coolant section emerging radially out of said sleeve.

8. The dental handtool as defined in claim 1, wherein said first coolant section inside said driving part emerges from the side of said driving part facing the handtool.

* * * * *